US009474714B2

United States Patent
Fabregas Vidal et al.

(10) Patent No.: US 9,474,714 B2
(45) Date of Patent: Oct. 25, 2016

(54) SOLID PHARMACEUTICAL COMPOSITION OF CATION EXCHANGE RESIN

(71) Applicant: LABORATORIOS RUBIO, S.A., Castellbisbal (ES)

(72) Inventors: Jose Luis Fabregas Vidal, Barcelona (ES); Joaquin Gomez Tomas, Hospitalet de Llobregat (ES); Nuria Ruiz Xiville, Badalona (ES)

(73) Assignee: LABORATORIOS RUBIO, S.A., Castellbisbal (ES)

( * ) Notice: Subject to any disclaimer, the term of this patent is extended or adjusted under 35 U.S.C. 154(b) by 0 days.

(21) Appl. No.: 14/419,372

(22) PCT Filed: Jul. 31, 2013

(86) PCT No.: PCT/ES2013/070565
§ 371 (c)(1),
(2) Date: Feb. 3, 2015

(87) PCT Pub. No.: WO2014/020222
PCT Pub. Date: Feb. 6, 2014

(65) Prior Publication Data
US 2015/0174065 A1    Jun. 25, 2015

(30) Foreign Application Priority Data

Aug. 3, 2012  (ES) .................... 201231270

(51) Int. Cl.
| | |
|---|---|
| A61K 9/00 | (2006.01) |
| A61K 31/795 | (2006.01) |
| A61K 33/06 | (2006.01) |
| A61K 33/00 | (2006.01) |
| A61K 9/14 | (2006.01) |

(52) U.S. Cl.
CPC ............ *A61K 9/0095* (2013.01); *A61K 9/146* (2013.01); *A61K 31/795* (2013.01); *A61K 33/00* (2013.01); *A61K 33/06* (2013.01)

(58) Field of Classification Search
None
See application file for complete search history.

(56) References Cited

U.S. PATENT DOCUMENTS

| 7,067,116 B1 | 6/2006 | Bess et al. | |
|---|---|---|---|
| 2004/0126324 A1* | 7/2004 | Hughes | ............... A61K 9/2013 424/10.1 |
| 2012/0107381 A1 | 5/2012 | Reddy et al. | |

FOREIGN PATENT DOCUMENTS

| EP | 0 976 408 | * | 2/2000 |
|---|---|---|---|
| EP | 0 976 408 A1 | | 2/2000 |
| EP | 1 031 345 A1 | | 8/2000 |
| WO | 2011/018801 A2 | | 2/2011 |
| WO | WO 2011/018801 | * | 2/2011 |
| WO | WO-2011/101734 | * | 8/2011 |

OTHER PUBLICATIONS

International Search Report, Application No. PCT/ES2013/070565, Dated: Dec. 11, 2013, 2 pages.
Search Report, Spanish Application No. P 201231270, Dated: Jul. 30, 2013, 1 page.

* cited by examiner

*Primary Examiner* — Frederick Krass
*Assistant Examiner* — Celeste A Roney
(74) *Attorney, Agent, or Firm* — Rothwell, Figg, Ernst & Manbeck P.C.

(57) ABSTRACT

The present invention relates to a solid pharmaceutical cation-exchange resin composition allowing the preparation of a stable resin suspension in an aqueous vehicle and the resin being easily resuspended in the case of sediment formation. Said composition comprises hydroxypropyl methylcellulose and pregelatinized starch as functional excipients. The invention also relates to a solid form for oral administration comprising the composition, to the use thereof for the preparation of oral solid forms, and to said composition for use in the treatment of hyperkalaemia.

17 Claims, 4 Drawing Sheets

SOLID PHARMACEUTICAL COMPOSITION OF CATION EXCHANGE RESIN

CROSS-REFERENCE OF THE RELATED APPLICATION

The present application is a 35 U.S.C. §371 National Phase Entry Application of PCT/ES2013/070565, filed 31 Jul. 2013, designating the United States, which in turn claims priority to Spanish Patent Application No. P 201231270, filed on 3 Aug. 2012, both of which are incorporated herein by reference.

FIELD OF THE ART

The present invention is encompassed in the field of the development of compositions comprising a cation-exchange resin for the treatment of hyperkalaemia.

PRIOR STATE OF THE ART

Potassium has several functions in the body: it regulates the activity of smooth muscles, cardiac muscles and skeletal muscles, takes part in enzymatic reactions involved in digestion and other metabolic processes in the body, and plays a role in homeostasis, the mechanism used by the body to maintain equilibrium between the many electrical and chemical processes in the body.

Almost all the potassium in the body is found intracellularly whereas only about 2% is found in extracellular fluids. Blood analyses show extracellular potassium levels and are not indicative of the amount of intracellular potassium. The movement of potassium into or out of cells can change the plasma potassium level, even though the total amount of potassium in the body does not change.

Hyperkalaemia is a hydroelectrolytic disorder which is defined when the high plasma potassium level is above about 5.5 mmol/l.

The causes of hyperkalaemia can be due to an increase in potassium intake, potassium redistribution, or a decrease in potassium renal excretion. The symptoms associated with hyperkalaemia are generally non-specific and include general discomfort, palpitations and muscle weakness. Very high potassium levels constitute a medical emergency since there is a risk of cardiac arrhythmias.

The treatments of hyperkalaemia include, for example, therapies with calcium gluconate, glucose-insulin, sodium bicarbonate, dialysis, or cation-exchange resins.

Therapy with cation-exchange resin is the most recommended therapy for daily potassium control in a hyperkalaemia situation resulting from chronic kidney failure. Said therapy involves eliminating potassium from the body by means of replacing potassium ions in the digestive tract with calcium or sodium ions coming from a cation-exchange resin, generally a polystyrene sulphonate resin.

In Europe, the recommended dose is 15 g of calcium polystyrene sulphonate up to three or four times a day. In the United States, the marketed product is sodium polystyrene sulphonate administered according to the same posology. However, in Japan and Korea, the accepted dose is 5 g of resin up to three times a day.

Polystyrene sulphonate resin is usually administered orally in the form of suspension in water. It must be taken into account that the resin is a powder practically insoluble in water having a tendency to settle quickly. Furthermore, given that the resin must be taken in a large amount in order to reach the dose at which the treatment becomes effective, the patient experiences a prolonged unpleasant feeling in his/her buccal cavity when consuming same. This is translated into a low degree of compliance with the indications of the prescription with respect to taking the medicament according to the recommended dosage regimen.

Therefore, problems in hyperkalaemia therapy with cation-exchange resins lie mainly in the difficulty of preparing a sufficiently stable resin suspension, the difficulty of resuspending the resin in the case of sediment formation, and the poor palatability due to repeated oral consumption of a high dose of resin throughout the day (every 8 hours).

Different approaches to overcome one or more of the mentioned problems have been described in the state of the art.

European patent application EP-A-0564154 describes formulations in the form of stable aqueous suspensions containing an ion-exchange resin (carrying a pharmaceutical active substance linked in the form of a resinate thereof), a thickening agent for increasing viscosity, and an amino acid acting as a dispersion stabilizer.

United States patent application US-A-2007/0248564 describes stable aqueous sodium polystyrene sulphonate suspensions which are ready-to-use and intended for the treatment of hyperkalaemia, comprising aluminium and magnesium silicate as a suspending agent and being sorbitol free.

International patent application WO-A-2010/132662 relates to powder compositions which comprise at least 40% potassium-binding active ingredient and are suitable for the treatment of hyperkalaemia. Particularly, it describes compositions containing a potassium-binding active ingredient, a suspending agent, a gliding agent, sorbitol and water.

European patent application EP-A-1004310 describes gelled aqueous compositions comprising an ion-exchange resin and one or more gelling agents.

European patent application EP-A-1031345 also describes gelled compositions. Said compositions comprise at least one gelling agent, water and a polystyrene sulphonate resin, having a mean particle size comprised between 5 and 100 µm. The compositions must be kept under cool conditions for obtaining the consistency of a gel, which complicates the production process. This document also describes the improvement in implementation which has been observed in some Japanese hospitals where the resin is administered in the form of a jelly preparation. However, it also indicates that said preparations have poor palatability.

European patent application EP-A-0976408 relates to formulations for the treatment of hyperkalaemia containing cation-exchange resins as an active ingredient, sodium carboxy methylcellulose as a gelling agent and hydroxypropyl cellulose as a binder. Said formulations are in the form of powder or granules which must be taken after suspending same in water. This document underlines the problems of poor palatability of such drugs and aims to prepare a new formulation that can be readily dispersed in water, said dispersion furthermore does not form aggregates after preparation and can be easily resuspended if a precipitate is formed. The assessment of the palatability of said compositions was performed by suspending 3.7 g, corresponding to 3.3 g of cation-exchange resin, in 33 ml of water, corresponding to the posology commonly used in Japan. These compositions have the drawback that they have a high viscosity when used under European conditions (15 g of resin in 100 ml of water) and that they contain sodium ions, which is not advisable in general and not for patients with kidney failure either.

The product SPS® Suspension, which is a sodium polystyrene sulphonate resin suspension in sorbitol, a high density liquid used for stabilizing the suspension, is available on the market of the United States. However, Chaudhury, et al., Am. J. Kidney Dis., 1997, 30(1), 120-122, described that the concomitant use of said resin and sorbitol can cause intestinal necroses.

None of the proposed solutions solves satisfactorily the problems in oral administration of ion-exchange resins for the treatment of hyperkalaemia.

Therefore, there is a need to provide a composition for the oral administration of ion-exchange resins which allows the formation of a stable resin suspension once it is constituted, easy resuspension in the case of sediment formation, improved palatability and absence of sodium ions, so that the patient will successfully comply with the prescribed dosage regimen.

DISCLOSURE OF THE INVENTION

The object of the present invention is a solid pharmaceutical composition comprising a cation-exchange resin as an active ingredient.

Another object of the invention relates to said composition for use in the treatment of hyperkalaemia.

Another object of the invention relates to the use of said composition for preparing solid forms of a cation-exchange resin for oral administration.

Another object of the invention is a solid form for oral administration comprising said composition.

DETAILED DESCRIPTION OF THE INVENTION

The object of the invention is a solid pharmaceutical composition comprising a cation-exchange resin, hydroxypropyl methylcellulose and pregelatinized starch.

The authors of the present invention have developed a solid pharmaceutical composition comprising a cation-exchange resin as an active ingredient which surprisingly allows the preparation of a stable resin suspension which is easily resuspended in the case of sediment formation and has an improved palatability and is substantially free of sodium ions.

Said composition helps the patient who is subjected to chronic therapy using cation-exchange resins to have a higher degree of compliance.

In a particularly preferred embodiment, the solid pharmaceutical composition consists essentially of a cation-exchange resin, hydroxypropyl methylcellulose and pregelatinized starch.

In the context of the invention, the expression "consists essentially of" limits the scope of the claim to the subject matters mentioned therein and to the subject matters that do not physically affect the basic characteristics of the composition of the invention. In this sense, it is understood that the composition can comprise other excipients such as sweetening agents, flavouring agents, or coloring agents, for example.

Flavouring agents and sweetening agents can be incorporated into the composition to enhance flavour and/or hide possible unpleasant flavours.

In a preferred embodiment, the solid pharmaceutical composition further comprises a flavouring agent and optionally a sweetening system.

The sweetening system can be formed by one or more sweetening agents.

The flavouring agent can be selected from the group consisting of, for example, mixed fruit flavouring, pineapple, strawberry, raspberry, banana, orange, lemon, lime, apricot, peach, cherry, liquorice, mint, vanilla, chocolate, coffee, and combinations thereof.

The content of flavouring agent in the composition of the invention can be comprised between 0.1% and 1% by weight with respect to the total weight of the composition, and preferably between 0.25% and 0.75%.

The sweetening agent making up the sweetening system can be selected from the group consisting of, for example, fructose, xylitol, sucrose, sucralose, glucose, maltose, stevioside, mannitol, thaumatin, neohesperidin dihydrochalcone (Neo-DHC), aspartame, saccharine, cyclamate, and combinations thereof.

The content of sweetening system in the composition of the invention can be comprised between 0.05% and 0.5% by weight with respect to the total weight of the composition, and preferably between 0.1% and 0.2%.

Cation-Exchange Resin

In the composition of the invention the active ingredient is a cation-exchange resin.

In the context of the invention, the cation-exchange resin is preferably selected from the group consisting of calcium polystyrene sulphonate and sodium polystyrene sulphonate.

In a preferred embodiment, the resin is sodium polystyrene sulphonate.

In another preferred embodiment, the resin is calcium polystyrene sulphonate.

Sodium or calcium polystyrene sulphonate is a polymer the basic unit of which is sulphonated styrene (vinylbenzene) in the form of sodium salt or calcium salt. It is generally cross-linked with a bifunctional monomer, such as divinylbenzene, for example. Said polymer has the functionality of acting as a cation-exchange resin, such that as it circulates through the intestine after oral administration, the calcium or sodium ions are partially substituted with potassium ions with the subsequent release of calcium or sodium ions.

Cation-exchange resins are available on the market, for example, under the name Amberlite® (Carlo Erba).

The polymers described in international patent application WO-A-2010/132662 can also be used as a cation-exchange resin.

In the composition of the invention, the content of cation-exchange resin is usually comprised between 95.0% and 99.8% by weight with respect to the total weight of the composition, preferably between 95.5% and 98.5%, more preferably between 96.0% and 97.5%, and even more preferably between 96.5% and 97.0%.

Hydroxypropyl Methylcellulose

Hydroxypropyl methylcellulose (hereinafter HPMC) is a cellulose which is partially methylated and partially 2-hydroxypropylated in the hydroxyl groups forming same.

HPMC is available in various grades with varied viscosity and extent of substitution. Generally, the various grades are distinguished from one another by the apparent viscosity of an aqueous solution of 2% HPMC by weight expressed in mPa·s and determined at 20° C.

The specifications of the different types of HPMC are described, for example, in the manual by R. C. Rowe et al., *Handbook of Pharmaceutical Excipients*, 4$^{th}$ edition, Pharmaceutical Press, London, 2003 [ISBN: 0-85369-472-9], for example.

HPMC is an excipient commonly used in pharmaceutical compositions for oral and topical administration. It is used in the preparation of tablets as a binder and also for modulating active ingredient release rate. It can be used in liquid as a viscosifying agent and suspending agent to inhibit sediment formation.

HPMC is available on the market through various companies under the names Methocel® (Dow), Benecel® (Ashland), Metolose® (Shin-Etsu), Pharmacoat® (Shin-Etsu), Tylopur® (Shin-Etsu), or Spectracel® (Sensient).

In the composition of the invention, HPMC selected from the 2208 types (USP) having an apparent viscosity comprised between 100-140,000 cps, more preferably comprised between 80,000-120,000 cps, and even more preferably an apparent viscosity of about 100,000 cps, is preferably used.

In the composition of the invention, the content of HPMC is usually comprised between 0.1% and 2.5% by weight with respect to the total weight of the composition, preferably between 0.75% and 2.25%, and more preferably between 1.25% and 2.0%, and even more preferably between 1.4% and 1.8%.

Pregelatinized Starch

Pregelatinized starch is a starch which has been treated by means of chemical or mechanical processes for partially or completely breaking the starch granules and converting starch into compressible fluid starch. The starch can be obtained from corn, rice or potatoes.

Pregelatinized starch typically comprises 5% free amylose, 15% free amylopectin, and 80% non-modified starch.

Specifications of the pregelatinized starch are described, for example, in the aforementioned manual by R. C. Rowe et al.

Pregelatinized starch is commonly used as a binder in the preparation of tablets in percentages greater than 5% with respect to the total weight of the composition, being able to reach up to 20%.

The pregelatinized starch is available on the market through various companies under the names Lycatab® (Roquette), Merigel® (Tate&Lyle), National® (National Starch), Unipure® (National Starch), PharmaGel® (Staple Food Products), Prejel® (DFE Pharma), Sepistab® (Seppic), or Spress® (GPC).

In the composition of the invention, the content of pregelatinized starch is usually comprised between 0.1% and 2.5% by weight with respect to the total weight of the composition, preferably between 0.75% and 2.25%, and more preferably between 1.25% and 2.0%, and even more preferably between 1.4% and 1.8%.

In the composition of the invention the sum of the percentages by weight of the components is adjusted to 100% and they refer to the percentage by weight with respect to the total weight of the composition.

In a preferred embodiment, the composition of the invention comprises between 95% and 97.5% by weight of cation-exchange resin, between 1.25% and 2.5% by weight of HPMC, and between 1.25% and 2.5% by weight of pregelatinized starch.

In a more preferred embodiment, the composition of the invention comprises between 95% and 97.5% by weight of cation-exchange resin, between 1.25% and 2.5% by weight of HPMC, between 1.25% and 2.5% by weight of pregelatinized starch, between 0.1% and 1% by weight of a flavouring agent and between 0.05% and 0.5% by weight of a sweetening system.

Surprisingly, the incorporation of the combination of pregelatinized starch and HPMC to a solid cation-exchange resin composition allows the preparation of a resin suspension in an aqueous vehicle which is substantially stable for normal administration, which is easily resuspended in the case of sediment formation, which has an improved palatability and which furthermore is substantially sodium ion free.

Said composition is suitable for the treatment of hyperkalaemia and a higher degree of compliance by the patient is thereby achieved due to its good sensorial characteristics.

Another object of the invention relates to said composition for use in the treatment of hyperkalaemia.

Solid Forms for Oral Administration

An object of the invention is the use of the composition of the invention for preparing solid forms of a cation-exchange resin for oral administration.

Another object of the invention is a solid form for oral administration comprising a therapeutically effective amount of the composition of the invention.

Given the characteristics of the medicament and the amount thereof that must be taken for it to be effective, the solid forms for oral administration are presented in the form of a unit dose or in a bulk package for unit dosing when administered to the patient.

In a preferred embodiment, the solid form for oral administration is a unit dose, and more preferably the unit dose is contained in a package in the form of a single-dose sachet.

The package can be, for example, a glossy paper, or a heat sealed plastic and aluminium laminate. The sachet is preferably formed by a plastic and aluminium laminate since it provides high protective quality and can be used in high speed packaging machines.

In a preferred embodiment, the unit dose comprises an amount of cation-exchange resin comprised between 5 g and 20 g, preferably between 10 g and 18 g, more preferably between 14 g and 16 g, and even more preferably 15 g; an amount of HPMC comprised between 0.08 g and 0.33 g, preferably between 0.17 g and 0.30 g, more preferably between 0.23 g and 0.27 g, and more preferably between 0.24 g and 0.26 g; and an amount of pregelatinized starch comprised between 0.08 g and 0.33 g, preferably between 0.17 g and 0.30 g, more preferably between 0.23 g and 0.27 g, and more preferably between 0.24 g and 0.26 g.

In a more preferred embodiment, the unit dose comprises 15 g of cation-exchange resin, 0.25 g of HPMC and 0.25 g of pregelatinized starch.

In an even more preferred embodiment, the unit dose comprises 15 g of cation-exchange resin, 0.25 g of HPMC, 0.25 g of pregelatinized starch, 0.10 g of flavouring agent, preferably banana flavouring, and a combination of 0.02 g of sucralose, and 0.01 g of Neo-DHC as a sweetening system.

Said unit dose is administered by suspending the content thereof in an amount of water comprised between 50 ml and 150 ml, preferably between 70 ml and 120 ml, more preferably between 80 ml and 110 ml, and even more preferably in 100 ml.

As mentioned above, the composition of the invention can also be presented in a suitable bulk package, such as a wide mouth glass or plastic bottle, for example, along with a spoon suitable for facilitating the correct dosing of the required amount of the composition of the invention.

Rheological Tests

In one test, aqueous suspensions were prepared from unit doses of a composition of the invention and of the compositions prepared following the wet kneading/granulation method described in Examples 1 and 2 of patent application EP-A-0976408, as described in the Examples section.

Figure 1:
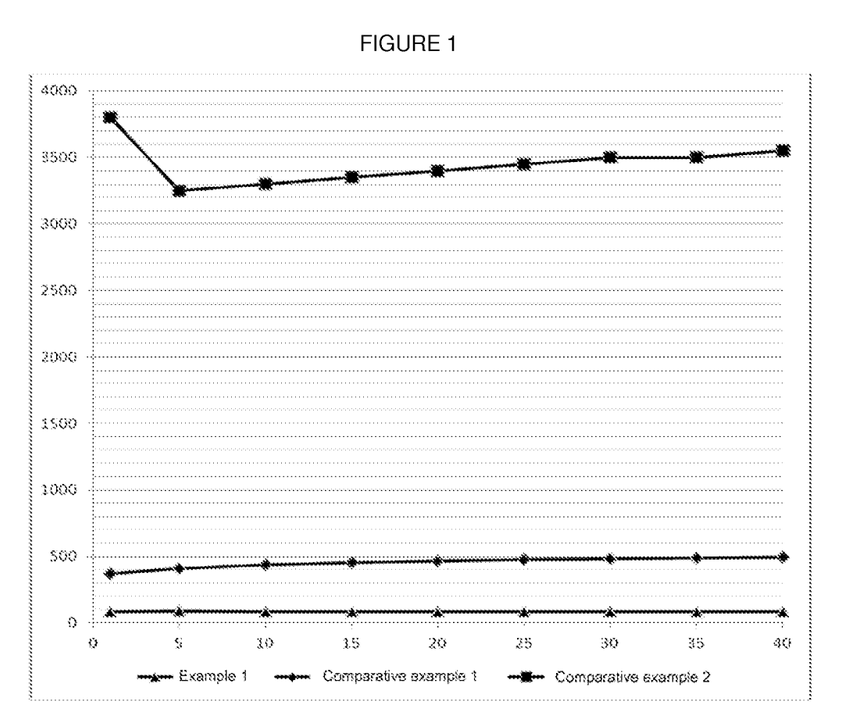
FIG. 1 depicts the viscosity of aqueous suspensions obtained when incorporating a unit dose of the compositions prepared in Example 1 and in comparative Examples 1 and 2 in 100 ml of water. The y-axis represents viscosity expressed in mPa·s and the x-axis represents time elapsed since adding water to the sample expressed in minutes.

FIG. 1 shows that the compositions described in the state of the art have a viscosity which is much higher than that considered appropriate for oral administration, and significantly higher than the viscosity of the composition of the invention which has a viscosity below or close to 100 mPa·s and which is suitable for oral administration.

In another test, aqueous suspensions were prepared from unit doses of the composition of the invention and of compositions that contained neither HPMC nor pregelatinized starch, or of compositions that contained only HPMC or pregelatinized starch, as described in the Examples section.

Figure 2:
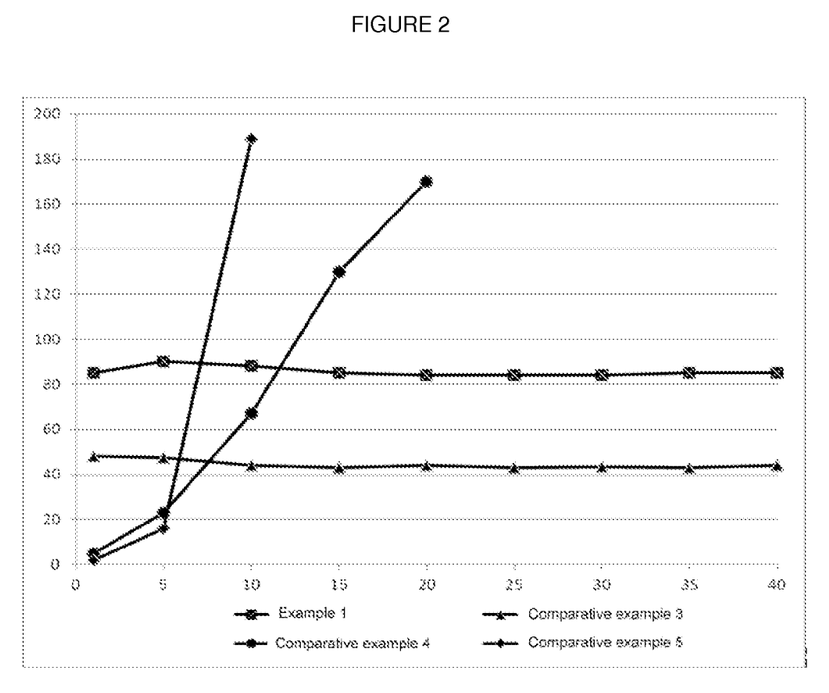
FIG. 2 depicts the viscosity of aqueous suspensions obtained when incorporating a unit dose of the compositions prepared in Example 1 and in comparative Examples 3 to 5 in 100 ml of water. The y-axis represents viscosity expressed in mPa·s and the x-axis represents time expressed in minutes.

When analyzing the viscosity values at the initial moments of the preparation of the suspension, FIG. 2 shows that when the formulation does not include HPMC, the presence of pregelatinized starch in the formulation has virtually no influence on the viscosity at 1 minute, whereas said starch has a significant effect in the presence of HPMC. This is translated into a synergistic effect of the combination of pregelatinized starch and HPMC on the viscosity of the suspension in the initial moments and at least up to 15 minutes.

The same FIG. 2 also shows that in compositions not comprising HPMC, there is massive sedimentation of the cation-exchange resin, whereas the composition of the invention has an initial viscosity of about 80 mPa·s which is kept substantially stable for a time not less than 15 minutes, and substantially constant up to 40 minutes. It is also seen that the viscosity recorded for the composition containing only hydroxypropyl methylcellulose as an excipient is significantly lower than that obtained with the composition of the invention.

Therefore, it can be concluded that, surprisingly, the combination of HPMC and pregelatinized starch of the composition of the invention allows the preparation of a cation-exchange resin suspension almost instantaneously and it is stable for at least up to 15 minutes.

Resuspension Tests

Aqueous suspensions were prepared from unit doses of compositions of the invention (Examples 1 and 2) and of compositions containing only HPMC or pregelatinized starch, and of compositions not containing HPMC or pregelatinized starch (comparative Examples 3, 4 and 5).

The suspensions were prepared by dispersing the compositions in a specific amount of water at a ratio of one unit dose per 100 ml of water; they were kept under stirring for a time of 2 minutes and then left standing for 1 hour.

The viscosity of the suspension was then determined by means of a viscometer for identifying the exact break point of the solid sediment which is related with the force necessary for initiating sediment resuspension, i.e., an indication of the starting force necessary for putting the spindle of the viscometer into operation.

Figure 3:
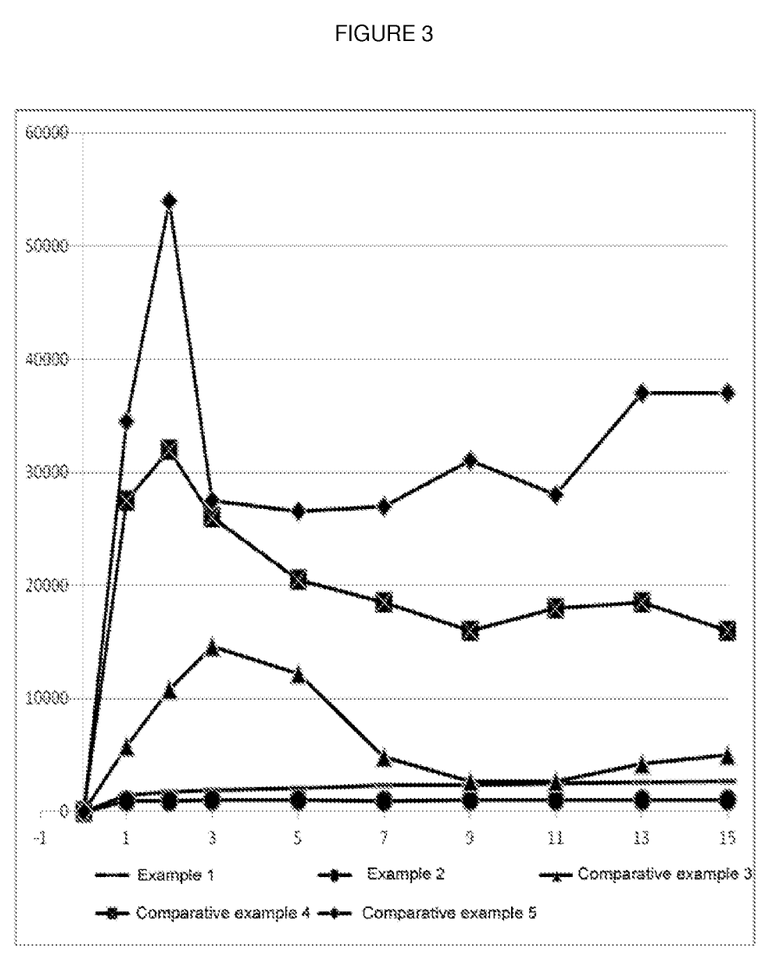
FIG. 3 depicts the viscosity of aqueous suspensions obtained when incorporating a unit dose of the compositions prepared in Examples 1 and 2 and in comparative Examples 3 to 5 in 100 ml of water after standing for one hour. The y-axis represents viscosity expressed in mPa·s and the x-axis represents time expressed in minutes. A maximum viscosity value offering an indication of the starting force necessary for putting the spindle of the viscometer into operation can be identified in this figure.
Figure 4:
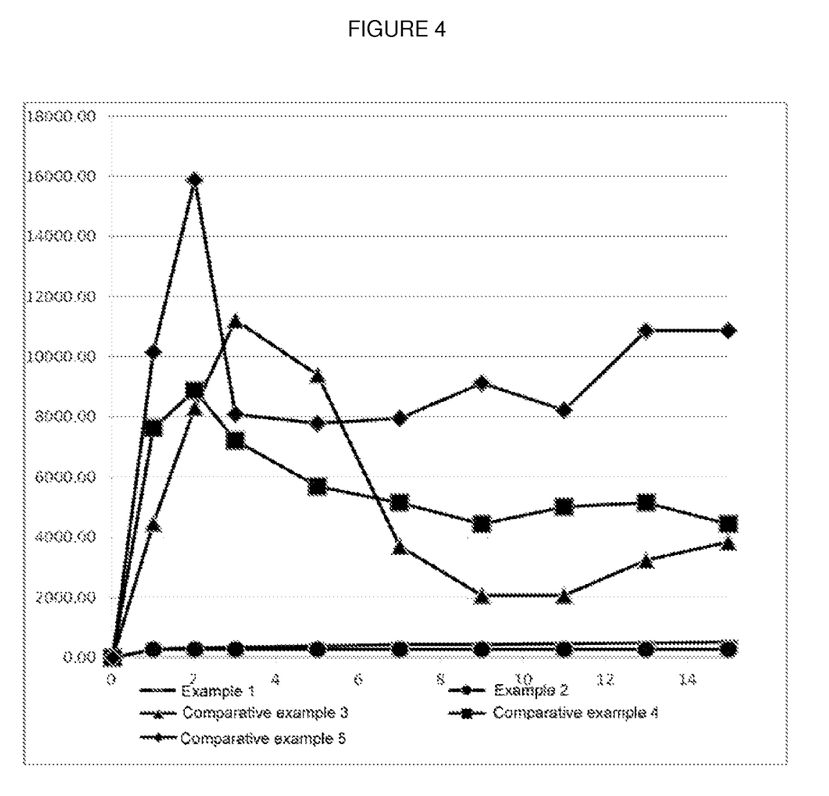
FIG. 4 depicts the viscosity of aqueous suspensions obtained when incorporating a unit dose of the compositions prepared in Examples 1 and 2 and in comparative Examples 3 to 5 in 100 ml of water after standing for one hour. The y-axis represents normalized viscosity expressed in mPa·s/cm and the x-axis represents time expressed in minutes. The normalized viscosity is the result of dividing the viscosity by the height of the resin sediment. Normalization is carried out to eliminate the influence of said height on the force necessary for putting the spindle of the viscometer into operation.

It was seen (FIG. 3) that the combination of pregelatinized starch and HPMC of the composition of the invention leads to a viscosity at the break point that is significantly lower than that seen when only one of the excipients is used or when no excipient whatsoever is used. The same effect can be seen in FIG. 4 showing the normalized viscosity expressed in mPa·s/cm which is the result of dividing the viscosity by the height of the resin sediment.

Therefore it can be concluded that, surprisingly, the combination of HPMC and pregelatinized starch of the composition of the invention leads to the formation of cation-exchange resin suspensions with a significant resuspension capacity.

Sensorial Test

A suspension prepared with 15.63 g of a composition of the invention according to Example 5 in 100 ml of water was assessed by a panel made up of people in relation to its organoleptic acceptability and their preference in comparison with a composition represented by that of comparative Example 5, flavoured with the presence of 0.04 g of vanilla essence per unit dose, or in other words a functional excipient (HPMC and pregelatinized starch) free cation-exchange resin composition.

The characteristics of the composition represented by Example 5 were assessed positively by the panellists, obtaining a good score. Therefore, concerning the acceptance of the organoleptic properties of the composition represented by Example 5, the panel determined they were 42% better than those of the composition represented by the flavoured comparative Example 5 as indicated, and 87% of the panel stated their preference for the composition of Example 5, again in comparison with that resulting from the flavoured comparative Example 5.

In a second test, the suspensions prepared with a unit dose (15 g of resin in 100 ml of water) of the compositions of Examples 1 and 2 of patent application EP-A-0976408 (comparative Examples 1 and 2) had a high viscosity. This characteristic contributed to the negative assessment thereof by the panellists in terms of how easy they are to consume. Furthermore, a significant portion of the medicament remained in the glass, the use of an additional amount of water for taking it being necessary, which increases the daily liquid intake, mainly in the daily administration regimen of every 8 hours, and is unsuitable for patients with kidney failure.

Therefore, it can be concluded that the compositions of the invention obtain a good sensorial assessment by the patients, which can contribute to a greater degree of compliance with the prescribed dosage regimen.

The following examples are shown to provide the person skilled in the art a sufficiently clear and complete explanation of the present invention, but they must not be considered as limiting the essential aspects of the object thereof, as mentioned in the preceding sections of this description.

EXAMPLES

Comparative Example 1

Preparation of the Composition of Example 1 of Patent Application EP-A-0976408

A composition containing 15.00 g of calcium polystyrene sulphonate resin and 1.5 g of sodium carboxy methylcellulose (1900 mPa·s at 2%) per unit dose was prepared following the wet kneading/granulation method described in Example 1 of patent application EP-A-0976408.

Comparative Example 2

Preparation of the Composition of Example 2 of Patent Application EP-A-0976408

A composition containing 15.00 g of calcium polystyrene sulphonate resin, 0.25 g of sodium carboxy methylcellulose (1900 mPa·s at 2%), 1 g of medium viscosity hydroxypropyl cellulose (5000 mPa·s at 2%), 0.02 g of aspartame and 0.01 g of methylcellulose (90 mPa·s) per unit dose was prepared following the wet kneading/granulation method described in Example 2 of patent application EP-A-0976408.

Comparative Example 3

Preparation of a Resin Composition with Hydroxypropyl Methylcellulose as a Functional Excipient 15.00 kg of calcium polystyrene sulphonate resin and 0.25 kg of hydroxypropyl methylcellulose were incorporated in a tumbler mixer, and the direct mixture thereof was performed at room temperature until obtaining a homogenous composition.

Comparative Example 4

Preparation of a Resin Composition with Pregelatinized Starch as a Functional Excipient A composition containing 15.00 kg of calcium polystyrene sulphonate resin and 0.25 kg of pregelatinized starch was prepared following a method similar to that of comparative Example 3.

Comparative Example 5

Preparation of a Resin Composition without Functional Excipients

A hydroxypropyl cellulose free composition containing 15.00 kg of calcium polystyrene sulphonate resin was prepared following a method similar to that of comparative Example 3.

Example 1

Preparation of the Composition 15.00 kg of calcium polystyrene sulphonate resin, 0.25 kg of hydroxypropyl methylcellulose, and 0.25 kg of pregelatinized starch were incorporated in a tumbler mixer.

It was mixed at room temperature until obtaining a homogenous composition.

The composition was packaged in sachets containing 15.5 g of composition.

Example 2

Preparation of the Composition

A composition containing 15.00 kg of calcium polystyrene sulphonate resin, 0.125 kg of hydroxypropyl methylcellulose, and 0.125 kg of pregelatinized starch was prepared following a method similar to that described in Example 1.

The composition was packaged in sachets containing 15.25 g of composition.

Example 3

Preparation of the Composition

A composition containing 15.00 kg of sodium polystyrene sulphonate resin, 0.25 kg of hydroxypropyl methylcellulose, and 0.25 kg of pregelatinized starch was prepared following a method similar to that described in Example 1.

The composition was packaged in sachets containing 15.5 g of composition.

Example 4

Preparation of the Composition

A composition containing 15.00 kg of sodium polystyrene sulphonate resin, 0.125 kg of hydroxypropyl methylcellulose, and 0.125 kg of pregelatinized starch was prepared following a method similar to that described in Example 1.

The composition was packaged in sachets containing 15.25 g of composition.

Example 5

Preparation of the Composition

A composition containing 15.00 kg of calcium polystyrene sulphonate resin, 0.25 kg of hydroxypropyl methylcellulose, 0.25 kg of pregelatinized starch, 0.1 kg of banana flavouring, 0.02 kg of sucralose and 0.01 kg of Neo-DHC was prepared following a method similar to that described in Example 1.

The composition was packaged in sachets containing 15.63 g of composition.

Example 6

Determination of the Viscosity of the Resin Compositions

Aqueous suspensions were prepared from the unit doses of the compositions prepared in Example 1 and in comparative Examples 1 and 2 in 100 ml of water. Each unit dose contained 15 g of cation-exchange resin.

The viscosity was determined using a Brookfield LVT6 viscometer equipped with the #1 spindle and at a constant speed of 30 rpm.

FIG. 1 shows that the compositions described in the state of the art (comparative Examples 1 and 2) had a viscosity which was much higher than that considered appropriate for oral administration, and significantly higher than the viscosity of the composition of the invention of Example 1.

The composition of comparative Example 1 had a viscosity of about 3500 mPa·s, the composition of comparative Example 2 a viscosity of about 500 mPa·s, whereas the composition of the invention of Example 1 had a viscosity below or close to 100 mPa·s, which is suitable for oral administration.

Example 7

Determination of the Initial Viscosity of the Resin Compositions

Aqueous suspensions were prepared from unit doses of the compositions prepared in Example 1 and in comparative Examples 3 to 5 at a ratio of one unit dose for every 100 ml of water. Each unit dose contained 15 g of cation-exchange resin.

The suspensions were prepared by pouring the equivalent of five unit doses of the corresponding formulation into a vessel containing 500 ml of water. Once prepared, the suspensions were kept under stirring at 600 rpm for 2 minutes.

The viscosity was determined using a Brookfield LVT6 viscometer Equipped with the #1 spindle and at a constant speed of 30 rpm.

The tested compositions can be included in the $2^2$ factorial design of Table I. Said table shows the compositions that have been tested, the excipients forming them and the viscosities of the aqueous suspensions thereof determined at 1 minute once the 600 rpm stirring period ended:

TABLE I

| Composition | Pregelatinized starch | HPMC | Viscosity (mPa · s) |
|---|---|---|---|
| Comparative Example 5 | No | No | 2 |
| Comparative Example 4 | Yes | No | 5 |
| Comparative Example 3 | No | Yes | 48 |
| Example 1 | Yes | Yes | 85 |

The disposition of the results according to this design allows observing easily the synergistic effect of the combination of pregelatinized starch and HPMC. It can be seen that when the formulation does not include HPMC, the presence of pregelatinized starch in the formulation has virtually no influence on viscosity at 1 minute, whereas it has a significant effect in the presence of HPMC. This is translated into a synergistic effect of the combination of pregelatinized starch and HPMC on the viscosity of the suspension in the initial moments and at least up to 15 minutes, and substantially constant up to 40 minutes.

FIG. 2 depicts the results obtained in this example.

It can be seen therein that the composition of the invention prepared in Example 1 has an initial viscosity of about 80 mPa·s which is kept substantially stable for a time not less than 15 minutes. The increase in viscosity seen in the case of the suspensions prepared from the compositions of comparative Examples 4 and 5 does not actually correspond with an increase in viscosity, but rather with the sedimentation of the resin which stops the spindle of the viscometer.

It is seen that the composition not containing any excipient whatsoever (comparative Example 5) settles en masse starting from minute 5.

It is also seen that the composition containing only pregelatinized starch as a functional excipient (comparative Example 4) is not capable of generating a viscosity sufficient for keeping the resin in suspension, such that the behaviour of this composition is substantially similar to that of the composition of comparative Example 5.

It can be seen that the viscosity recorded for the composition of comparative Example 3 containing only hydroxypropyl methylcellulose as an excipient is significantly lower than that obtained with the composition of the invention.

Example 8

Determination of the Resuspension Capacity of the Resin Compositions

Aqueous suspensions were prepared from unit doses of the compositions prepared in Examples 1 and 2 and in comparative Examples 3 to 5 at a ratio of one unit dose for every 100 ml of water. Each unit dose contained 15 g of cation-exchange resin.

The suspensions were prepared by pouring the equivalent of five unit doses of the corresponding formulation into a vessel containing 500 ml of water. Once prepared, the suspensions were kept under stirring at 600 rpm for 2 minutes and were then left standing for 1 hour.

The viscosity was determined using a Brookfield LVT6 viscometer equipped with the #1 spindle and at a constant speed of 0.3 rpm for the suspensions prepared from the compositions of Example 1 and of comparative Example 3, and with the #2 spindle for the compositions of comparative Examples 4 and 5, also using the speed of 0.3 rpm. The use of different spindles results from the different volumes of precipitates formed according to the tested composition.

By means of using the speed of 0.3 rpm, the exact break point of the solid sediment can be determined with greater precision, offering a reference of the force necessary for initiating sediment resuspension, i.e., an indication of the starting force necessary for putting the spindle of the viscometer into operation.

Similarly to what was done in Example 7, the tested compositions and the results can be included in the $2^2$ factorial design with the central point shown in Table II. Said table includes the compositions that have been tested, the excipients forming them and the viscosity of the break point for each of the aqueous suspensions:

TABLE II

| Composition | Pregelatinized starch (g/unit dose) | HPMC (g/unit dose) | Viscosity (mPa · s) |
|---|---|---|---|
| Comparative Example 5 | 0 | 0 | 54000 |
| Comparative Example 4 | 0.25 | 0 | 22000 |
| Comparative Example 3 | 0 | 0.25 | 14600 |

TABLE II-continued

| Composition | Pregelatinized starch (g/unit dose) | HPMC (g/unit dose) | Viscosity (mPa · s) |
|---|---|---|---|
| Example 1 | 0.25 | 0.25 | 2000 |
| Example 2 | 0.125 | 0.125 | 1000 |

It can be seen that the combination of pregelatinized starch and HPMC of Examples 1 and 2 leads to a viscosity at the break point that is significantly lower than that observed when only one of the excipients is used. FIG. 3 depicts the viscosity results obtained for each of the tested compositions. The maximum of each of the curves offers an indication of the force necessary in each case for putting the spindle of the viscometer into operation, which in turn is a reference to how easily the sediment is resuspended.

This influence is clearly shown to a greater extent if the viscosity at the break point is normalized to the same volume of sediment, as shown in Table III. Said table includes the height of the container and the normalized viscosity at the break point for each of the tested compositions:

TABLE III

| Composition | Preg. starch (g/unit dose) | HPMC (g/unit dose) | Viscosity (mPa · s) | Height (cm) | Normalized viscosity (mPa · s/cm) |
|---|---|---|---|---|---|
| Comparative Example 5 | 0 | 0 | 54000 | 3.4 | ~15900 |
| Comparative Example 4 | 0.25 | 0 | 22000 | 3.6 | ~8900 |
| Comparative Example 3 | 0 | 0.25 | 14600 | 1.3 | ~11200 |
| Example 1 | 0.25 | 0.25 | 2000 | 5.4 | 370 |
| Example 2 | 0.125 | 0.125 | 1000 | 3.7 | 270 |

The results of Table III indicate that, beyond the variability inherent to the precision of the method, the combination of pregelatinized starch and HPMC significantly reduces the force necessary for resuspending a settled aqueous cation-exchange resin suspension compared with the use of each of the excipients separately.

FIG. 4 depicts the normalized viscosities obtained in this Example 8 for the tested compositions.

It can be seen therein that the compositions of the invention prepared in Examples 1 and 2 have a normalized viscosity at the break point that is significantly lower than that obtained in the case of the compositions containing only one of the functional excipients or none at all.

It is seen that the composition not containing any functional excipient whatsoever (comparative Example 5) has a normalized viscosity at the break point equal to about 16000 mPa·s/cm.

It can be seen that the normalized viscosity at the break point is equal to about 11200 mPa·s/cm recorded for the composition of comparative Example 3 containing only HPMC as a functional excipient.

It is also seen that the composition containing only pregelatinized starch (comparative Example 4) as a functional excipient has a normalized viscosity at the break point of about 8900 mPa·s/cm.

Therefore, it is inferred from this test that the compositions of the invention comprising the combination of HPMC and pregelatinized starch have a considerable resuspension capacity.

The invention claimed is:

1. A solid pharmaceutical composition comprising hydroxypropyl methylcellulose (HPMC), pregelatinized starch, and a cation-exchange resin selected from the group consisting of calcium polystyrene sulphonate and sodium polystyrene sulphonate, wherein the cation-exchange resin is the only therapeutically effective active ingredient in the composition.

2. The composition according to claim 1, characterised in that it further comprises a flavouring agent and optionally a sweetening system.

3. The composition according to claim 1, characterised in that the resin is calcium polystyrene sulphonate.

4. The composition according to claim 1, characterised in that the resin is sodium polystyrene sulphonate.

5. The composition according to claim 1, characterised in that the content of cation-exchange resin is comprised between 95.0% and 99.8% by weight with respect to the total weight of the composition.

6. The composition according to claim 1, characterised in that the content of hydroxypropyl methylcellulose is comprised between 0.1% and 2.5% by weight with respect to the total weight of the composition.

7. The composition according to claim 1, characterised in that it comprises between 95.0% and 97.5% by weight of cation-exchange resin, between 1.25% and 2.5% by weight of HPMC, and between 1.25% and 2.5% by weight of pregelatinized starch.

8. The composition according to claim 2, characterised in that it comprises between 0.1% and 1% by weight of a flavouring agent and between 0.05% and 0.5% by weight of a sweetening system.

9. The composition according to claim 1 for use in the treatment of hyperkalaemia.

10. A solid form for oral administration characterised in that it comprises a therapeutically effective amount of the composition according to claim 1.

11. The solid form according to claim 10, characterised in that it is presented in the form of a unit dose or in a bulk package for unit dosing when administered to the patient.

12. The solid form according to claim 11, characterised in that the unit dose is contained in a package in the form of a single-dose sachet.

13. The solid form according to claim 12, characterised in that it comprises an amount of cation-exchange resin comprised between 5 g and 20 g, an amount of HPMC comprised between 0.08 g and 0.33 g, and an amount of pregelatinized starch comprised between 0.08 g and 0.33 g.

14. The solid form according to claim 13, characterised in that it comprises 15 g of cation-exchange resin, 0.25 g of HPMC and 0.25 g of pregelatinized starch.

15. The solid form according to claim 14, characterised in that it further comprises 0.1 g of flavouring agent, and a combination of 0.02 g of sucralose and 0.01 g of neohesperidin DC as sweetening system.

16. The solid form according to claim 1, wherein the ratio of the hydroxypropyl methylcellulose to pregelatinized starch is 1:1.

17. The composition according to claim 1, wherein the pregelatinized starch is present in an amount ranging between 0.1% and 2.5% by weight with respect to the total weight of the composition.

* * * * *